US00PP37067P2

(12) United States Plant Patent
Wezelenburg, Jr.

(10) Patent No.: US PP37,067 P2
(45) Date of Patent: Oct. 28, 2025

(54) ***CERCIDIPHYLLUM* PLANT NAMED 'JWW11'**

(50) Latin Name: *Cercidiphyllum japonicum*
Varietal Denomination: JWW11

(71) Applicant: Jan-Willem Wezelenburg, Jr., Hazerswoude-Dorp (NL)

(72) Inventor: Jan-Willem Wezelenburg, Jr., Hazerswoude-Dorp (NL)

(73) Assignee: JAN-WILLEM WEZELENBURG BOSKOOP B.V., Hazerswoude-Dorp (NL)

( * ) Notice: Subject to any disclaimer, the term of this patent is extended or adjusted under 35 U.S.C. 154(b) by 0 days.

(21) Appl. No.: 19/208,214

(22) Filed: May 14, 2025

(51) Int. Cl.
*A01H 5/00* (2018.01)
*A01H 6/00* (2018.01)

(52) U.S. Cl.
USPC ..... Plt./216
CPC ..... *A01H 6/00* (2018.05)

(58) Field of Classification Search
USPC ..... Plt./216
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Cercidiphyllum* plant named 'JWW11', that is characterized by its compact, upright, even, and nearly globular plant habit, its dark red young foliage that matures to green to dark red, new foliage emerging throughout the season is dark red, its branches that are red in color in winter, its well branched growth habit, and its easy propagation by grafting.

2 Drawing Sheets

Botanical classification: *Cercidiphyllum japonicum.*
Variety denomination: 'JWW11'.

CROSS REFERENCE TO A RELATED APPLICATION

This application is related to a European plant breeders' rights application filed on May 18, 2021, application No. 2021/1295. Information for the plant breeders' rights application was received from the Inventor.

BACKGROUND OF THE INVENTION

The present invention relates to a new and distinct cultivar of *Cercidiphyllum japonicum* and will be referred to hereafter by its cultivar name, 'JWW11'. 'JWW11' is a new cultivar of Katsura tree for use as an ornamental landscape plant.

The Inventor selected the new cultivar as a seedling in a seedbed at his nursery in Hazerswoude-Dorp, The Netherlands in May of 2016. The seedbed had been planted with seeds collected (and pooled) from open pollinated unnamed and unpatented proprietary seedlings of *Cercidiphyllum japonicum* from the Inventor's breeding program. The exact parents are unknown.

Asexual propagation of the new cultivar was first accomplished by the Inventor by grafting onto *Cercidiphyllum japonicum* seedling rootstock (not patented) in May of 2018 in Hazerswoude-Dorp, The Netherlands. Asexual propagation by grafting has determined that the unique characteristics of the new cultivar are stable and reproduced true to type in successive generations.

SUMMARY OF THE INVENTION

The following traits have been repeatedly observed and represent the characteristics of the new cultivar. These attributes in combination distinguish 'JWW11' as a unique cultivar of *Cercidiphyllum.*

1. 'JWW11' exhibits a compact, upright, even, and nearly globular plant habit.
2 'JWW11' exhibits dark red young foliage that matures to green to dark red, new foliage emerging throughout the season is dark red.
3. 'JWW11' exhibits branches that are red in color in winter.
4. 'JWW11' exhibits a well branched growth habit.
5. 'JWW11' exhibits easy propagation by grafting.

'JWW11' can be most closely compared to the *Cercidiphyllum* cultivars 'Rotfuchs' (not patented) and 'Peach' (not patented). 'Rotfuchs' is similar to 'JWW11' in having a compact plant habit. 'Rotfuchs' differs from 'JWW11' in having a slower growth habit and dark purple-red color foliage when young and mature. 'Peach' is similar to 'JWW11' in having an upright plant habit. 'Peach' differs from 'JWW11' in having foliage that is green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Jardins du Florilege, Cieplucha, Van Vliet New Plants (a catalog of new introductions they represent, but not a sales catalog), Floravert, Pepiniere du Vent Val, Bluebell Arboretum & Nursery, Kurowscy, Floramedia, Pepiniere, Esveld, Zahradnictvi Spomysl, Bambuscentrum, Fragaria, Taobao, Kurowscyskolki, Kledzik, and Bambuscentrum.

BRIEF DESCRIPTION OF THE DRAWINGS

The accompanying color photographs illustrate the overall appearance and distinct characteristics of the new *Cercidiphyllum*. The photographs were taken of a one-year-old plant of the new cultivar as grown outdoors in 2-liter containers in Hazerswoude-Dorp, The Netherlands.

The photograph in FIG. 1 provides a side view of the overall plant habit of 'JWW11'.

Figure 1:
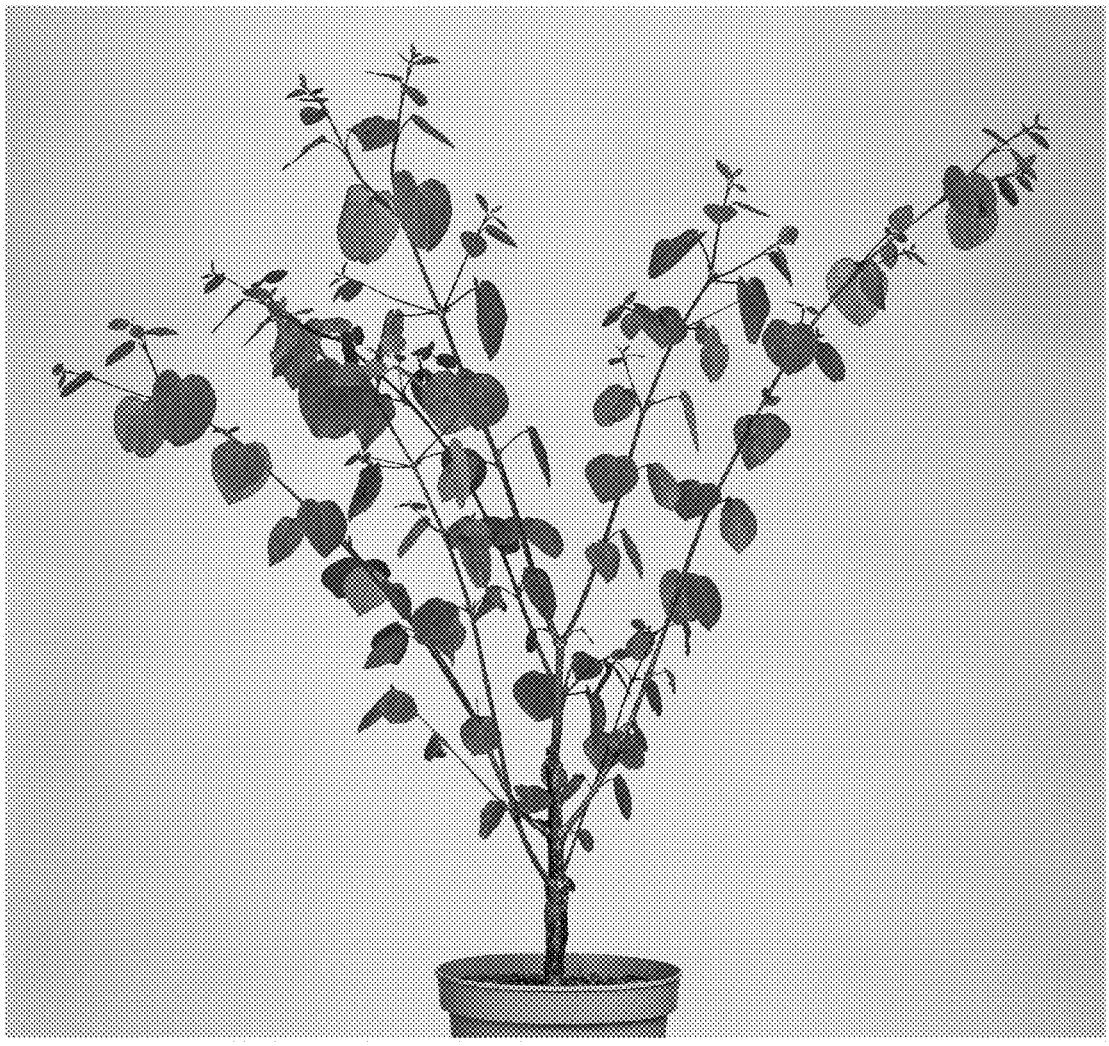
Figure 2:
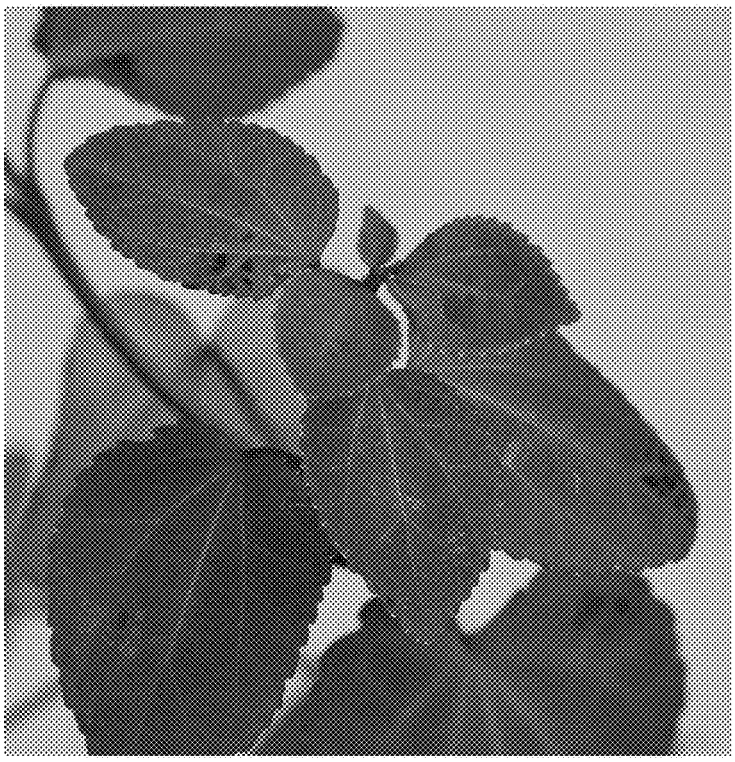

The photograph in FIG. 2 provides a close-up view of the young foliage of 'JWW11'.

Figure 3:
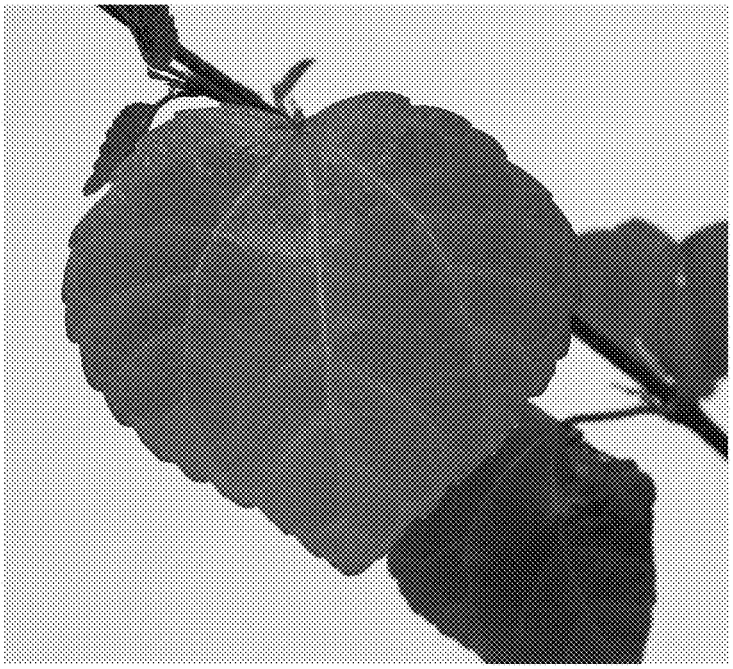

The photograph in FIG. 3 provides a close-up view of the mature foliage and stems of 'JWW11'.

The colors in the photographs are as close as possible with the photographic and printing technology utilized and the color values cited in the detailed botanical description accurately describe the colors of the new *Cercidiphyllum*.

DETAILED BOTANICAL DESCRIPTION

The following is a detailed description of one-year-old plants of the new cultivar as grown outdoors in 2-liter containers in Hazerswoude-Dorp, The Netherlands. The color determination is in accordance with the $6^{th}$ Edition, 2019 Reprint of 2015 Colour Chart of The Royal Horticultural Society, London, England, except where general color terms of ordinary dictionary significance are used.

General description:

*Plant type*.—Deciduous shrub.

*Plant habit*.—Compact, upright, even, and nearly globular plant habit.

*Plant size*.—Average of 59 cm in height, 50.6 cm in spread as a one-year-old plant in a container, an average of 6 m in height, 1.5 m in spread as grown in the landscape.

*Cold hardiness*.—At least in U.S.D.A. Zone 5.

*Diseases and pests*.—No Susceptibility or resistance to diseases or pests has been observed.

*Root description*.—Fibrous and fine.

*Growth rate*.—Slow and moderately vigorous.

Branch description:

*Branch shape*.—Round.

*Branch color*.—Young; a blend of 178A and 185A, base of connection 145A, mature; N199B, occasionally tinged 178A, lenticels, approximately 3 mm in diameter, 199D, older and winter; N200A.

*Branch size*.—An average of 33.9 cm in length, 2 mm in diameter.

*Branch surface*.—Matte.

*Branch aspect*.—Held at an average angle of 50° to main stem.

*Branch strength*.—Very strong.

*Branching*.—Free branching, an average of 6 lateral branches.

*Internode length*.—An average of 5.8 cm.

Foliage description:

*Leaf shape*.—Cordate.

*Leaf division*.—Simple.

*Leaf base*.—Obtuse to undeeply truncate or very short acuminate.

*Leaf apex*.—Obtuse to slightly acute.

*Leaf fragrance*.—A pleasant "burnt sugar" like fragrance, typical for *Cercidiphyllum* present in autumn when leaves have dropped.

*Leaf venation*.—Laciniate, color; upper surface 183C, lower surface 176C.

*Leaf margins*.—Finely serrate, no undulation.

*Leaf arrangement*.—Opposite, alternate on strong growing shoots.

*Leaf attachment*.—Petiolate.

*Leaf aspect*.—Flat.

*Leaf surface*.—Glabrous, both sides matte, very slightly leathery.

*Leaf size*.—An average of 4.3 cm in length and 4 cm in width.

*Leaf quantity*.—An average of 12 per lateral branch.

*Leaf color*.—Young upper surface; a blend of 183A and N186C, main veins 175C, young lower surface; 195A, main veins and secondary veins 175C, edged 185A, mature upper surface; 177A, area around main veins and occasionally around secondary veins 152A, mature lower surface; a blend of 148C and N148B, thinly edged 185A, mature fall color both surfaces; a blend of 19B and 23C.

*Petioles*.—An average of 2.2 mm in length and 1 mm in width, color; upper surface 185A, proximal end occasionally N144C, lower surface 180A, proximal end N144C.

*Stipules*.—None.

Inflorescence/fruit description: No flowers or fruit have been observed to date, the species bears blooms on older plants and are insignificant.

It is claimed:

1. A new and distinct cultivar of *Cercidiphyllum* plant named 'JWW11' as herein illustrated and described.

* * * * *